| United States Patent [19] | [11] | 4,382,040 |
|---|---|---|
| Parr | [45] | May 3, 1983 |

[54] PROCESS FOR PRODUCTION OF 2,3-DIMERCAPTOPROPANE-1-SULFONIC ACID AND ITS SALTS

[75] Inventor: Wolfgang Parr, Berlin, Fed. Rep. of Germany

[73] Assignee: Heyl & Co., Berlin, Fed. Rep. of Germany

[21] Appl. No.: 178,588

[22] Filed: Aug. 15, 1980

[30] Foreign Application Priority Data

Aug. 16, 1979 [DE] Fed. Rep. of Germany ....... 2933027

[51] Int. Cl.$^3$ ........................................... C07C 143/22
[52] U.S. Cl. .................................................. 260/513 R
[58] Field of Search ....................... 260/513 R, 504 R

[56] References Cited

PUBLICATIONS

Gilbert, "Sulfonation and Related Reactions", (1965), pp. 136–145.
Wagner, "Synthetic Organic Chem.", (1965), pp. 106, 778.
Chem. Abst., vol. 51, Nos. 5692i–5693q.
Johary et al, J. Chem. Soc., pp. 1307–1311, London, (1955).

*Primary Examiner*—Alan Siegel
*Attorney, Agent, or Firm*—Schwartz, Jeffery, Schwaab, Mack, Blumenthal & Koch

[57] ABSTRACT

A process for producing 2,3-dimercaptopropane-1-sulfonic acid or its salts useful as an antidote to toxic metal salt poisoning comprising reacting an allyl bromide with sodium sulfite in aqueous medium at a temperature from 50 to 100 degrees C. to produce sodium-2-propene-1-sulfonate, brominating the 2-propene-1-sulfonate, eliminating excess bromine by adding sodium sulfite, adjusting the Ph to 4.5 with sodium hydroxide, reacting the brominated compound with sodium hydrogen sulfide in an alkaline medium to produce sodium-2,3-dimercaptopropane-1-sulfonate, precipitating the raw product as a lead salt or mercury, cadmium, tin, copper, nickel, cobalt or zinc complex, suspending the precipitated product in methanol and reacting it with gaseous hydrogen sulfide, adjusting the Ph of the solution with a solid bicarbonate selected from the group consisting of sodium bicarbonate, ammonium bicarbonate and potassium bicarbonate to a Ph of 4.5, filtering out precipitated metal sulfides, isolating the raw product by evaporating the filtrate to dryness, and recrystallizing the raw product in a 90% solution of ethanol or isopropanol.

15 Claims, No Drawings

PROCESS FOR PRODUCTION OF 2,3-DIMERCAPTOPROPANE-1-SULFONIC ACID AND ITS SALTS

BACKGROUND OF THE INVENTION

This invention relates to a process for producing 2,3-dimercaptopropane-1-sulfonic acid having the formula

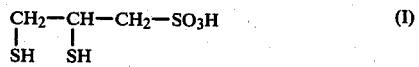

and its salts.

2,3-dimercaptopropane-1-sulfonic acid and its salts are useful in treating cases of poisoning by highly toxic metal salts. This is particularly true of the sodium salt (hereafter abbreviated as Na-DMPS). Among the metal toxins which may be treated are mercury, cadmium and lead salts. These compounds are also effective in treating poisoning by antimony and arsenic compounds. Compounds produced according to the process of the invention, especially Na-DMPS, exhibit a high therapeutic index and have a substantially lower toxicity than other antidotes which are utilized in treating poisoning by the aforementioned agents.

M. S. Johary and L. N. Owen, J. Chem. Soc. (London) 1307 (1955) describe the production of Na-DMPS by reacting a 2,3-dibromopropane-1-sulfonic acid intermediate with sodium thioacetate. A disadvantage of this procedure is the fact that sodium thioacetate is very expensive. Additionally, this known procedure produces neither pure products or satisfactory yields. However, in view of the aforementioned utility of 2,3-dimercaptopropane-1-sulfonic acid and its salts, it is of substantial importance to obtain pure products; and in view of the exceptional effectiveness of these compounds and the limited capacity of known processes to produce them, there is additionally a need for a process for making such compounds which enables the achievement of economically viable yields of very pure product.

It is an object of the present invention to provide a process for making 2,3-dimercaptopropane-1-sulfonic acid and its salts which produces high yields of pure product.

It is also an object of the invention to provide a process which is simple and can be carried out economically.

SUMMARY OF THE INVENTION

These objects are achieved by providing a process for making 2,3-dimercaptopropane-1-sulfonic acid comprising (a) reacting an allyl halide with a sulfite to form the corresponding 2-propene-1-sulfonate;

(b) brominating the product of step (a) to produce sodium-2,3-dibromopropane-1-sulfonate;

(c) converting the product of step (b) with an alkali solution of sodium hydrogen sulfide to sodium-2,3-dimercaptopropane-1-sulfonate;
either (d) precipitating the product of step (c) with $Pb^{+2}$ salts;
or (d') converting the product of step (c) to a salt of a cation selected from the group consisting of $Hg^{+2}$, $Cd^{+2}$, $Sn^{+2}$, $Cu^{+2}$, $Ni^{+2}$, $Co^{+2}$, and $Zn^{+2}$ and then precipitating the product with alcohol;

(e) decomposing the product of step (d) or step (d') by reacting with hydrogen sulfide;

(f) isolating the resulting 2,3-dimercaptopropane-1-sulfonic acid or salt thereof; and (g) recrystallizing the recovered product from a 90% alcohol solution.

In the process of the invention, it is especially advantageous to carry out the reaction with hydrogen sulfide in step (e) in anhydrous medium. It is also advantageous to carry out the reaction in a 10-fold amount of alcohol, especially methanol, with gaseous hydrogen sulfide.

After the reaction of step (e), it is preferred to adjust the Ph to a value from 4.0 to 5.5, most preferably 4.5. Desirably, the adjustment of the Ph is effected with solid sodium bicarbonate or ammonium bicarbonate depending upon the desired salt.

It is also preferred to isolate the 2,3-dimercaptopropane-1-sulfonic acid or salt thereof by evaporating the filtrates obtained in step (f) to dryness under vacuum.

Desirably, the recrystallization in step (g) is effected with 90% ethanol or isopropanol; most preferably with a 10-fold amount of 90% ethanol.

It is advantageous to carry out the precipitation in step (d') after adjusting the Ph to about 4.5. Preferably the precipitation of step (d') is effected with 40 to 70% methanol solution. According to a particularly preferred procedure, the precipitation is initiated with heat and thereafter completed with a 50% methanol solution.

Preferably in step (a) allyl bromide is reacted with sodium sulfite to form sodium-2-propene-1-sulfonate. It is also preferred in step (b) to remove excess bromine by adding sodium sulfite.

The reaction of step (c) is advantageously carried out over a period of from about 10 to 30 hours at temperatures from about 0 to about 40 degrees C., most preferably at room temperature.

It is further preferred to conduct the reaction of step (a) in water at a temperature of from about 50 to about 100 degrees C.

Desirably, in step (b) after removal of the excess bromine, the Ph is adjusted with sodium hydroxide to a value from 4.5 to 8.

Preferred metal salts are lead acetate, mercury-II chloride, cadmium chloride, tin chloride or zinc sulfate. The most preferred reagent is a solution of mercury-II chloride in methanol.

The salts of 2,3-dimercaptopropane-1-sulfonic acid embraced by the invention include especially the pharmaceutically acceptable salts such as sodium, potassium or ammonium salts, the salts of primary, secondary and tertiary amines such as methyl amine, dimethyl amine, trimethyl amine, ethyl amine, diethyl amine, polycationic salts and salts of other physiologically unobjectionable inorganic or organic cations.

It is believed, that in the conversion in step (d) of the process of the invention, the sodium dimercaptopropane sulfonic acid and the lead-II salt form a double salt of the following formula

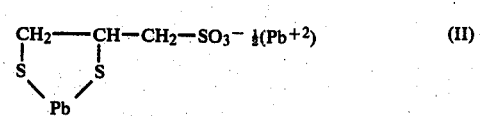

It is believed that in step (d') of the process of the invention, a complex is formed having the following formula

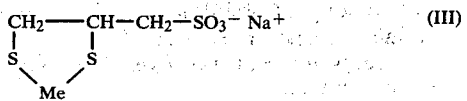

wherein Me represents Hg+2, Cd+2, Sn+2, Cu+2, Ni+2, Co+2, or Zn+2.

The process of the invention avoids the disadvantages of the prior known processes. Products are obtained in very good yields having a purity which meets the requirements for the intended pharmaceutical uses.

The process of the invention can be carried out in a single vessel. Thus, the excess bromine in step (b), of the process of the invention is removed by reduction with sodium sulfite instead of by distillation. As a result, the reaction for forming the 2,3-dibromopropane-1-sulfonic acid is quickly completed, thereby producing substantial energy savings. To avoid foaming, the neutralization is effected with caustic soda lye instead of sodium carbonate.

In the process of the invention, it has been determined as a result of kinetic investigations, that the SH-group exchange reaction is completed after 24±5 hours at room temperature with a maximum yield of 2,3-dimercaptopropane-1-sulfonic acid. Higher temperatures and longer reaction times always lead to formation of undesired byproducts, chiefly mixed disulfides and tetrasulfides, which reduce the final yield and which because of their chemical and physical characteristics cannot be separated from the final product without substantial difficulty.

The process of the invention has the advantage, composed to the prior state of the art, that the precipitated lead salt obtained as an intermediate product is quickly available, and analytic tests show it to be almost free of impurities. For further processing, the lead salt is suspended in a 10-fold amount of alcohol, methanol being especially preferred, and reacted with hydrogen sulfide. The precipitated lead sulfide is removed by filtration and extracted with methanol to improve the ultimate yield. The Ph of the combined filtrates is adjusted with sodium bicarbonate to Ph 4.5. The filtrate is then evaporated to dryness under vacuum to obtain the raw product. The resulting raw product contains a dimercaptopropane sulfonic acid content of greater than 82%.

In this embodiment of the process of the invention, it is important that the lead salt is reacted with hydrogen sulfide in an alcoholic medium. By using an alcoholic medium, one obtains a quantum increase in yield and purity in comparison to working with an aqueous medium.

It is especially advantageous in the process of the invention to carry out the recrystallization of the raw product in an alcohol-water mixture, preferably 90% ethanol or 90% isopropanol in order to obtain an especially pure product. It is possible in a simple manner to obtain a pharmaceutically pure final product if the initial raw product is recrystallized from a 10-fold amount by weight of 90% ethanol.

According to an alternate embodiment of the process of the invention, the conversion of the intermediate 2,3-dimercaptopropane-1-sulfonic acid is effected with metal-II salts of the hydrogen sulfide group, particularly mercury-II chloride, cadmium-II chloride, copper-II chloride and tin-II chloride and with metal-II salts of the ammonium sulfide group, in particular zinc-II sulfate, nickel-II chloride and cobalt-II chloride whereby the corresponding complexes having the formula III are subsequently isolated.

The metal-II dimercaptopropane sulfonic acid compounds obtained according to this embodiment of the process of the invention are all 1:1 complexes and, in contrast to the lead salts, are readily soluble in water. They are separated from the aqueous solution, after adjusting the Ph value to 4.5, by precipitating them with an alcohol in the presence of heat. Preferably the alcohol is methanol having an alcohol content of 40 to 70%, most preferably 50%. The precipitated material is separated by vacuum filtration and recrystallized from 50% methanol in order to separate any inorganic salts which may have been co-precipitated. The recrystallization is, however, not absolutely essential since the inorganic salts remain undissolved after the reaction with hydrogen sulfide. A particular advantage of this procedure is that it is possible in a simple manner to isolate stable metal complexes of dimercaptopropene sulfonic acid which in the production and further processing likewise contain toxicologically and ecologically unobjectionable metals.

For further processing, the metal-II DMPS complexes are worked up as described for the lead salts. In every case, one obtains dimercaptopropane sulfonic acid and/or the alkali salts thereof in crystalline form and pharmaceutically pure quality.

The invention will be further described with reference to the following examples.

EXAMPLE I

Production of the sodium salt of 2,3-dimercaptopropane-1-sulfonic acid:

(a) Pb-2,3-Pb-dimercaptopropane-1-sulfonate 121 grams (1.0 moles) freshly distilled allylbromide are refluxed with 139 grams (1.1 moles) sodium sulfite in 1 liter of water for a period of 4 hours until the mixture forms a single phase. The cold solution is extracted twice with hexane in order to remove unreacted allylbromide and the organic phase is discarded. Then, over a period of from 1½ to 2 hours, approximately 200 grams bromine are introduced at room temperature with rapid stirring until a yellow color is obtained. A tiny amount of sodium sulfite on the tip of a spatula is added to the weakly yellow solution in order to reduce excess bromine. The colorless solution (Ph 0.5) is adjusted with a 25% sodium hydroxide solution to a Ph of 6.5. Thereafter, 280 grams of a 29% sodium hydrogen sulfide solution, produced by saturating a 25% sodium hydroxide solution with hydrogen sulfide, are slowly added with stirring to the still warm solution. After a reaction period of 16 hours with stirring at room temperature, the mixture is adjusted to a Ph of 5 with concentrated acetic acid and excess hydrogen sulfide is removed under vacuum.

A sample is withdrawn, and the SH-group content therein is determined iodometrically (0.67 moles with respect to DMPS). Then 379 grams (1 mole) of lead acetate dihydrate are dissolved in 1.5 liters water and warmed to 60 degrees C. The reaction solution is likewise heated to 60 degrees C. and the lead acetate solution is added thereto with rapid stirring. Stirring is continued for 1 hour at 60 degrees C. after which the lead salt is removed by filtration, washed with water at a temperature of 60 degrees C. and then vacuum filtered. The moist lead salt is resuspended in 1 liter of water at 60 degrees C., stirred, filtered, washed with water and methanol, and finally dried.

Yield 222 grams, 66.8% of the theoretical with reference to the titrated dithiol.

Analysis: found 62% Pb, calculated 62.6% Pb.

(b) Sodium dimercaptopropane sulfonate (Na-DMPS)

222 grams of the lead salt are suspended in 2 liters of methanol, and while strongly stirring the suspension, hydrogen sulfide is introduced until the suspension is saturated. Precipitated lead sulfide is removed by filtration. To increase the ultimate yield of desired product, the lead sulfide is stirred with 500 milliliters of methanol and then filtered again. The combined filtrates are adjusted with sodium bicarbonate to a Ph of 4.5 after which hydrogen sulfide is again introduced. After regulating the Ph of the solution (Ph 4.5), the solution is filtered and the clear filtrate is evaporated to dryness under vacuum.

Yield 86.5 grams raw product (91.8% of the theoretical yield based on the lead salt).

Iodometric analysis: 88.3% SH.

The raw product is recrystallized from 865 milliliters of 90% ethanol and dried under vacuum to a constant weight.

Yield 65.0 grams (69.0% of the theoretical yield based on the lead salt, 46.2% of the theoretical yield based on the titrated dithiol).

| Elemental Analysis: | | | | |
| --- | --- | --- | --- | --- |
| | C | H | S | Na |
| Found | 17.29 | 3.33 | 45.5 | 10.57 |
| Calculated | 17.13 | 3.35 | 45.75 | 10.93 |

Iodometric analysis: 99.0% SH.

EXAMPLE II

Production of the ammonium salt of 2,3-dimercaptopropane-1-sulfonic acid:

30 grams of the lead salt of 2,3-dimercaptopropane-1-sulfonic acid produced as in Example I(a) are dissolved as in Example I(b) and the resulting clear filtrate is adjusted to a Ph of 4.5 with ammonium bicarbonate. The solution is filtered again, and the filtrate is evaporated to dryness under vacuum.

Yield: 8.1 grams raw product (65.3% of the theoretical yield based on the lead salt).

Iodometric analysis: 84.1% SH.

After recrystallization of the raw product in 90 milliliters of 90% isopropanol, 5.5 grams of product are obtained (44.4% of the theoretical yield based on the lead salt).

Iodometric analysis: 95.4% SH.

| Elemental analysis for $C_3H_{11}S_3O_3N$. | | | | |
| --- | --- | --- | --- | --- |
| | C | H | S | N |
| Found | 17.28 | 5.42 | 45.93 | 6.55 |
| Calculated | 17.55 | 5.40 | 46.85 | 6.82 |

EXAMPLE III

Production of the potassium salt of 2,3-dimercaptopropane-1-sulfonic acid:

Following the procedure set forth in Example I(b) and II and utilizing the same amounts of material, one obtains after adjusting the Ph value to 4.5 with potassium bicarbonate, 10 grams of raw product (73.2% of the theoretical yield based on the lead salt).

Iodometric analysis: 88.3% SH.

After recrystallizing the raw product in 100 milliliters of 87.5% isopropanol, 8 grams of potassium dimercaptopropane sulfonate (K-DMPS) are obtained (58.7% of the theoretical yield based on the lead salt; analysis 96.5%).

| Elemental analysis for $C_3H_7S_3O_3K$: | | | | |
| --- | --- | --- | --- | --- |
| | C | H | S | K |
| Calculated | 15.92 | 3.12 | 42.49 | 17.27 |
| Found | 16.09 | 3.11 | 40.9 | 17.10 |

EXAMPLE IV

Production of sodium dimercaptopropane sulfonic acid via a mercury complex:

(a) Na-2,3-Hg-dimercaptopropane-1-sulfonate

The procedure of Example I(a) is followed up to the attachment of the SH-groups. The dimercaptopropane sulfonate content of 1.4 liters of solution is iodometrically determined to be 0.55 moles. The solution is slowly reacted with 150 grams of mercury-II chloride dissolved in 400 milliliters of methanol. The solution then has a Ph of about 1. The Ph is adjusted to 4.5 with solid sodium bicarbonate. The clear solution is warmed to 60 degrees C., and 1 liter of methanol is added with vigorous stirring. The solution is then cooled, and the mercury complex is filtered out and dried. The raw yield was 207 grams.

To purify the raw product, 187 grams raw product were added to 1.7 liters of water, decomposed with 1.7 liters of methanol and dissolved with stirring and heat. After cooling, the mercury complex is removed by filtration and dried.

Yield: 157 grams (70% of the theoretical based on the titrated dithiol).

After two recrystallizations of a small sample in water/methanol, the elemental analysis for $C_3H_5S_3O_3HgNa$ was:

| | C | H | S | Hg | Na |
| --- | --- | --- | --- | --- | --- |
| Calculated | 8.81 | 1.23 | 23.53 | 45.06 | 5.62 |
| Found | 8.85 | 1.38 | 21.52 | 50.0 | 5.85 |

(b) Sodium dimercaptopropane sulfonate (Na-DMPS)

The mercury complex from Example IV(a) is suspended in 1.5 liters of methanol, and hydrogen sulfide is introduced with vigorous stirring until the solution is saturated. Precipitated mercury sulfide is removed by filtration. In order to increase the ultimate yield, the mercury sulfide is resuspended in 500 milliliters of methanol, stirred and removed by filtration. The combined filtrates are adjusted to a Ph of 4.5 with solid sodium bicarbonate, filtered again and evaporated to dryness under vacuum.

Yield: 67 grams raw product (82.9% of the theoretical yield based on the mercury complex).

Iodometric analysis 88.5% SH.

After recrystallization in 670 milliliters of 90% ethanol, 55.8 grams of DMPS are obtained (69.0% of the theoretical yield based on the mercury complex; 48.3% of the theoretical yield based on the titrated dithiol).

Iodometric analysis: 99.6% SH.

EXAMPLE V

Production of sodium dimercaptopropane sulfonate via a cadmium complex:

(a) Na 2,3-Cd-dimercaptopropane-1-sulfonate

To a 2 liter solution containing 0.38 moles of dimercaptopropane sulfonic acid (DMPS) are added dropwise with stirring 77 grams of cadmium chloride monohydrate (CdCl$_2$.1H$_2$O) dissolved in 100 milliliters of water. The Ph of the resulting solution is adjusted to 4.5 with solid sodium bicarbonate. The solution is warmed to 60 degrees and decomposed under strong stirring with 2.1 liters of methanol. After cooling, the resulting cadmium complex is removed by filtration, washed with methanol/water (50:50) and dried. The raw yield was 124 grams (the raw product contained inorganic salts).

After recrystallizing a sample in water/methanol (50:50), the elemental analysis for cadmium was 33.8% Cd (theoretical cadmium 35.05% Cd).

(b) Sodium dimercaptopropane sulfonate (Na-DMPS)

Using the method described in Example IV(b) and the same amounts of material, one obtains from the 124 grams of raw Na-2,3-Cd-dimercaptopropane-1-sulfonate 65 grams of raw product (81.4% of the theoretical yield based on the titrated dithiol).

Iodometric analysis: 81% SH.

After recrystallization in 650 milliliters of 90% ethanol, 39.5 grams of dimercaptopropane sulfonate (DMPS) are obtained (49.5% of the theoretical yield based on the titrated dithiol).

Iodometric analysis: 98.3% SH.

EXAMPLE VI

Production of sodium dimercaptopropane sulfonate (Na-DMPS) via a tin complex:

(a) Na-2,3-Sn-dimercaptopropane-1-sulfonate

The procedure of Example I(a) is followed up to the attachment of the SH-groups. The dithiol content of 2 liters of solution was determined iodometrically to be 0.42 moles dithiol. Following the procedure of Example V(a), but using 81.6 grams of tin-II chloride, the corresponding tin complex was produced.

Raw yield: 100 grams (the raw product still contains inorganic salts).

Analysis of a repeatedly recrystallized sample showed 37.52% Sn (theoretical value 36.3% Sn).

(b) Sodium dimercaptopropane sulfonate (Na-DMPS)

The tin complex is decomposed by reacting with hydrogen sulfide as described in Examples I(a) through V(a) and thereafter worked up to Na-DMPS according to the procedure of Example IV(b).

Yield: 58.5 grams raw product (66.3% of the theoretical yield based on the titrated dithiol).

Iodometric analysis: 83% SH.

After recrystallization in 585 milliliters of 90% ethanol, 42.1 grams DMPS are obtained (47.7% of the theoretical yield based on the titrated dithiol).

Iodometric analysis: 98.2% SH.

EXAMPLE VII

Production of Na-DMPS via a zinc complex:
(a) Na-2,3-Zn-dimercaptopropane-1-sulfonate The procedure of Example I(a) is followed up to the attachment of the SH-groups. In 2 liters of the resulting solution, the iodometrically determined content of dithiol amounted to 0.32 moles. Following the procedure described in Example V(a), a zinc complex is produced utilizing 92 grams zinc-II sulfate.

Yield: 104 grams raw product.

After recrystallization from water/methanol a metal analysis showed 23.47% Zn (theoretical analysis 23.89% Zn).

(b) Sodium dimercaptopropane sulfonate (Na-DMPS)

100 grams of zinc complex are suspended in 1 liter of methanol, made clearly alkaline with concentrated ammonia and decomposed by introducing hydrogen sulfide. The precipitated zinc sulfide is removed by filtration, stirred with 500 milliliters methanol, and the filtrates are combined. After acidifying with acetic acid to Ph 4.5, the resulting solution is evaporated to dryness.

Raw yield: 43 grams (63.9% of the theoretical yield based on titrated dithiol).

Iodometric analysis: 83.2% SH.

The raw product is recrystallized in 430 milliliters 90% ethanol.

Yield: 31.3 grams (46.6% of the theoretical yield based on titrated dithiol).

Iodometric analysis 97.5% SH.

The foregoing description and examples have been set forth merely by way of exemplification, and not by way of limitation. Since modifications of the specifically disclosed procedures may occur to persons skilled in the art, the scope of the invention is to be limited solely by the scope of the appended claims.

I claim:

1. Process for production of 2,3-dimercaptopropane-1-sulfonic acid having the formula:

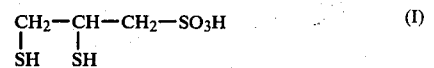

$$CH_2-CH-CH_2-SO_3H \qquad (I)$$
$$\phantom{CH_2-}|\phantom{CH-}|$$
$$\phantom{CH_2-}SH\phantom{CH}SH$$

and its salts comprising:
(a) reacting an allyl halide with a sulfite to form a corresponding 2-propene-1-sulfonate and thereafter extracting the resulting solution with a solvent to remove unreacted allyl halide;
(b) brominating the product of step (a) to produce sodium-2,3-dibromopropane-1-sulfonate and subsequently removing excess bromine with sodium sulfite and adjusting the pH of the solution with alkali to from 4.5 to 8;
(c) reacting the product of step (b) with sodium hydrogen sulfide at room temperature over a period of about 30 hours in alkaline medium to produce sodium-2,3-dimercaptopropane-1-sulfonate;
(d) forming a complex of sodium-2,3-dimercaptopropane-1-sulfonate from step (c) with a bivalent metal ion selected from the group consisting of mercury, cadmium, tin, copper, nickel, cobalt and zinc and precipitating the complex with alcohol;
(e) reacting the product of step (d) in methanol with hydrogen sulfide;
(f) adjusting the pH of the reaction mixture to a value from about 4.0 to about 5.5;
(g) isolating the resulting 2,3-dimercaptopropane-1-sulfonic acid or salt thereof; and (h) recrystallizing the product in an alcoholic medium selected from the group consisting of 90% ethanol and 90% isopropanol.

2. Process according to claim 1 wherein the reaction in step (e) with hydrogen sulfide is carried out in anhydrous medium.

3. Process according to claim 2 wherein the reaction is carried out in a 10 fold amount of methanol with gaseous hydrogen sulfide.

4. Process according to claim 1 wherein the adjustment of the pH in step (f) effected with a solid bicarbonate selected from the group consisting of sodium bicarbonate, ammonium bicarbonate and potassium bicarbonate.

5. Process according to claim 1 wherein the pH is adjusted in step (f) to about 4.5.

6. Process according to claim 1 wherein the 2,3-dimercaptopropane-1-sulfonic acid or salt thereof is isolated in step (g) by filtering the solution from step (f) and evaporating the filtrate to dryness under a vacuum.

7. Process according to claim 6 wherein the raw product is recrystallized from a 10 fold amount by weight of a 90% solution of an alcohol selected from the group consisting of ethanol and isopropanol.

8. Process according to claim 3 wherein the precipitation is effected after the pH has been adjusted to about 4.5.

9. Process according to claim 8 wherein the precipitation is effected by adding a 40 to 70% methanol solution.

10. Process according to claim 8 or 9 wherein the initial precipitation is effected from warm solution and the precipitate is subsequently recrystallized in a 50% methanol solution (50% methanol:50% water).

11. Process according to claim 1 wherein allyl bromide is reacted with sodium sulfite in step (a) to form sodium-2-propene-1-sulfonate.

12. Process according to claim 11 wherein the reaction of allyl bromide with sodium sulfite is effected in aqueous medium.

13. Process according to claim 12 wherein the reaction of allyl bromide with sodium sulfite is effected at a temperature from about 50 to about 100 degrees C.

14. Process according to claim 1 wherein the complex formation of step (d) is effected by adding a reagent selected from the group consisting of mercury-II chloride, cadmium chloride, tin chloride and zinc sulfate.

15. Process according to claim 14 wherein said complex formation is effected by adding a solution of mercury-II chloride in methanol.

* * * * *